United States Patent [19]

Klopotek

[11] Patent Number: 5,312,330
[45] Date of Patent: May 17, 1994

[54] MEDICAL TREATMENT OF THE EYE INVOLVING REMOVAL OF THE EPITHELIUM

[75] Inventor: Peter J. Klopotek, Framingham, Mass.

[73] Assignee: Summit Technology, Inc., Waltham, Mass.

[21] Appl. No.: 886,375

[22] Filed: May 20, 1992

[51] Int. Cl.⁵ .......................................... A61M 31/00
[52] U.S. Cl. .................................... 604/49; 604/22; 606/166; 128/898
[58] Field of Search ................ 604/22, 49; 606/166, 606/167, 180; 128/897, 898

[56] References Cited

U.S. PATENT DOCUMENTS

| | | |
|---|---|---|
| 3,818,913 | 6/1974 | Wallach . |
| 3,930,505 | 1/1976 | Wallach . |
| 3,990,453 | 11/1976 | Douvas et al. ........................ 606/107 |
| 3,996,935 | 12/1976 | Banko .................................... 604/22 |
| 4,019,514 | 4/1977 | Banko . |
| 4,024,866 | 5/1977 | Wallach . |
| 4,117,843 | 10/1978 | Banko . |
| 4,205,682 | 6/1980 | Crock et al. ......................... 606/166 |
| 4,273,127 | 6/1981 | Auth et al. ......................... 606/16 X |
| 4,320,761 | 3/1982 | Haddad ............................... 606/107 |
| 4,665,913 | 5/1987 | L'Esperance, Jr. . |
| 4,718,418 | 1/1988 | L'Esperance, Jr. . |
| 4,750,491 | 6/1988 | Kaufman et al. . |
| 4,770,172 | 9/1988 | L'Esperance, Jr. . |
| 4,798,204 | 1/1989 | L'Esperance, Jr. . |
| 4,816,018 | 3/1989 | Parisi . |
| 4,856,513 | 8/1989 | Muller . |
| 4,941,093 | 7/1990 | Marshall et al. . |
| 4,983,181 | 1/1991 | Civerchia . |
| 4,994,081 | 1/1991 | Civerchia et al. . |
| 5,074,862 | 12/1991 | Rausis .................................. 606/19 |
| 5,139,518 | 8/1992 | White .............................. 606/166 X |

FOREIGN PATENT DOCUMENTS 3707004  9/1988  Fed. Rep. of Germany ...... 606/166

OTHER PUBLICATIONS

McDonald, Marguerite, "Excimer Laser Corneal Surgery for the Comprehensive Ophthalmologist", Convention of American Academy of Ophthalmology, Oct. 13, 1991 transcript.

Primary Examiner—Randall L. Green
Assistant Examiner—Mary Beth O. Jones
Attorney, Agent, or Firm—Fish & Richardson

[57] ABSTRACT

A method and device for lifting the epithelium from a selected area of the eye using an incision instrument for cutting the epithelium to define an area of the epithelium to be removed, and a fluid jet assembly for separating the selected area of the epithelium from the underlying layer. The incision instrument shown has a series of incision elements distributed about a peripheral pattern, arranged to cut the epithelium in the direction of its thickness without disturbing the underlying layer, to create a tear line. The jet assembly directs through the tear line a fluid jet in the manner that the fluid progresses inwardly from the tear line and effectively wedges the epithelium from the underlying layer. The device shown also has an epithelium support structure for engaging the exterior surface of the delineated area of the epithelium in order to support and maintain the structural integrity of the lifted epithelium. The lifted epithelium can be biologically preserved and repositioned after a medical procedure is conducted on the exposed surface of the eye. Isotonic fluids for maintaining the biological balance of the eye tissue and use of softening agents for aiding in the release of scarred or tenaciously held epithelium are also disclosed.

7 Claims, 8 Drawing Sheets

MEDICAL TREATMENT OF THE EYE INVOLVING REMOVAL OF THE EPITHELIUM

BACKGROUND OF THE INVENTION

This invention relates to removal of the epithelium during medical treatment of the eye.

The cornea comprises transparent avascular tissue that forms the anterior portion of the eye. It resides in the sclera at the limbus. The cornea functions as both a protective membrane and a "window" through which light passes as it proceeds to the retina. The transparency of the cornea is due to its uniform structure, avascularity, and deturgescence, which is the state of relative hydration of the corneal tissue. The average adult cornea is about 0.65mm thick at the periphery and about 0.54 mm thick in the center. From anterior to posterior, the cornea has the following five distinct layers: the epithelium, Bowman's membrane, the stroma, Descemet's membrane, and the endothelium. The present invention concerns the epithelium, Bowman's membrane and the stroma. The epithelium consists of five or six layers of cells, and the underlying Bowman's membrane, a clear acellular layer, is a modified portion of the stroma. The corneal stroma accounts for about 90 percent of the corneal thickness. The stroma is composed of intertwining lamellar fibers that are about 1 $\mu$m wide and run almost the full diameter of the cornea. They run parallel to the surface of the cornea and by virtue of their size and periodicity are optically clear.

The corneal epithelium encompasses a rich network of nerve fibers with bare ends. Whenever the nerve fibers are exposed, they produce a sensation of pain. Since the endings of the nerve fibers are located near the surface, severe pain results from even a minor abrasion of the corneal epithelium. The nutrition of the cornea including the epithelium is provided by the vessels of the limbus, the aqueous, and tears. The corneal epithelium also extracts most of its oxygen from the atmosphere.

Damage to the epithelium causes transient localized swelling of the corneal stroma that clears when the epithelium cells regenerate. The epithelium forms an effective barrier to the entrance of microorganisms into the cornea. If the epithelium is removed or traumatized, Bowman's layer and the avascular stroma become susceptible to a variety of microorganisms.

The epithelium layer consists of highly renewable cells which are capable of regrowth within a few days. Once formed, these cells define a highly organized light transparent unit.

Before any surgical procedure on the stroma can be conducted, the epithelium must first be removed. The surgical removal of the epithelium is currently performed by mechanically scraping the epithelium layer from the underlying layer. The precision and quality of this procedure depends upon the ophthalmologist's skill and also on the morphology of the eye surface, i.e., how firmly the epithelium is attached to Bowman's membrane and to the stroma and the health and condition of the epithelium. In particular, contact lens wearers and people who previously have undergone corneal sculpting often have the epithelium strongly attached to the underlying surface. Patients who have undergone prior injury or treatment might often have scar tissue. In such cases, mechanical epithelium removal is frequently nonuniform and requires considerable time to perform. Furthermore, since the procedure depends on the skill of the ophthalmologist, removal of the epithelium entails risk of damage to the Bowman's layer and to the stroma.

After eye surgery, it often takes 40 to 70 hours for the missing epithelium layer to regrow over the surface of the eye. It takes even longer for the epithelium cells to achieve coherent orientation and organization that allows full transparency and proper vision. This is not only a painful process, but the patient's vision is also impaired during this healing period.

It has been suggested that de-epithelization of the eye be performed using scraping or tearing by mechanical means, with or without the additional use of softening agents. However, with such techniques the epithelium is not removed uniformly and in any event the healing period and discomfort can remain a problem. It has also been suggested to replace removed epithelium cells back upon the eye after the eye surgery to assist in healing, but we are unaware that this has been done satisfactorily.

In summary, there continues to be a need for a surgical device and procedure which can remove the epithelium in a standardized manner, very quickly and without causing damage to the cornea and which enables rapid convalescence. In addition, there is a particular need for a device and procedure that enables removal of the epithelium which is strongly attached to the underlying layer, i.e., Bowman's membrane or stroma in cases wherein the Bowman's membrane was previously removed.

SUMMARY OF THE INVENTION

According to one aspect, the invention provides a standardized, uniform, rapid means of lifting the corneal epithelium in a selected area employing a fluid jet. Due to its short duration, high precision, and other attributes, the process in conjunction with bond weakening agents, can be used to remove scarred or strongly attached epithelium.

According to another aspect, lifting of the epithelium is accompanied by maintaining the structural integrity of the lifted epithelium layer, the epithelium is biologically preserved, and it is replaced upon the eye after the desired procedure has been performed on the underlying structure. During the lifting process the epithelium and the Bowman's layer can be continuously hydrated, which can serve to preserve both layers.

In another aspect, the invention is a system and method for removing the epithelium from a selected area of the eye utilizing an incision instrument for cutting the epithelium in the direction of its thickness in a peripheral pattern circumscribing the selected area of epithelium to be removed, and employing a jet assembly for directing, through the cut pattern in the epithelium, a fluid jet in the manner that the fluid progresses inwardly from the peripheral pattern between the epithelium and the relatively hard underlying layer (i.e., Bowman's layer or stroma in cases wherein the Bowman's layer was previously removed) to which the epithelium is adhered to effectively wedge the epithelium free from the underlying layer.

Preferred embodiments of this aspect of the invention include one or more of the following features.

The jet assembly is constructed and arranged to simultaneously direct the fluid inwardly at regions distributed about the peripheral pattern, preferably such jet system being combined with a support structure constructed and arranged to engage the exterior surface of the selected area of the epithelium in a manner to support and maintain the structural integrity of the epithelium freed from the underlying layer, and preferably the system also comprising means for biologically preserving the freed, structurally intact segment of the epithelium while a medical procedure is conducted on the exposed eye and thereafter returning the epithelium segment onto the eye in a manner to cause it to reattach as living cells integrated with the eye.

More generally, the invention may also include a support structure constructed and arranged to engage the exterior surface of the selected area of the epithelium while a wedging fluid jet is applied, and to maintain the structural integrity of the freed segment of the epithelium.

In preferred embodiments of either case employing a support structure, the support structure has one or more of the following features.

The support surface is arranged to be directed toward the eye in slightly spaced relationship to receive the freed segment.

The support structure comprises a compliant member defining a support surface, the compliance of the support member being selected to enable the surface to yield as the segment of epithelium is forced toward it by the water jet, thereby enabling progressive advance of the hydraulic wedge formed by the jet.

Preferred embodiments of the invention employ an incision instrument which comprises a reference member arranged to be positioned over and in contact with the eye, and an incision blade which is moveable between retracted and extended positions from within the reference member, the distance of projection being less than the thickness of the epithelium. Preferably, the incision blade is extended using energizing means and is adapted to be released from the retracted to the projected position. In various of the embodiments, preferably a plurality of incision blades are distributed about the peripheral pattern and arranged to simultaneously make a pattern of discrete small incisions to define the boundary of the epithelium to be removed. Preferably either the incision blades are mutually arranged to form substantially continuous peripheral tear line or the system includes means to rotate the incision blades to produce a substantially continuous peripheral tear line.

Other advantages and features of the invention will be apparent from the following description of the preferred embodiment and from the claims.

DESCRIPTION OF THE PREFERRED EMBODIMENT

Figure 1:
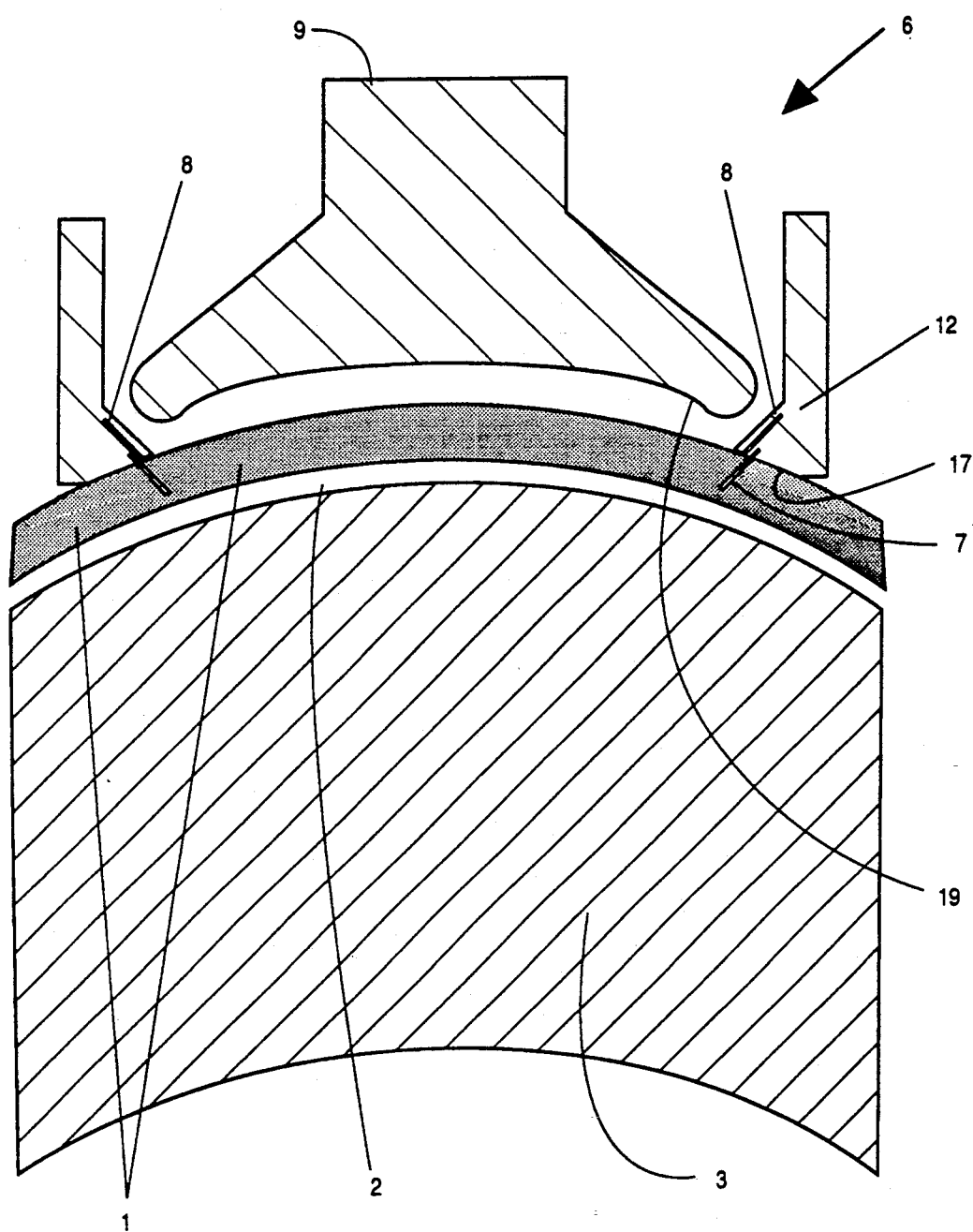
FIG. 1 is a diagrammatic cross-sectional view of an epithelium lifting device according to a preferred embodiment of the invention, shown in place over an eye.

Referring to FIG. 1, an epithelium lifting device 6 shown during the epithelium lifting process, comprises a main body 12, a plurality of incision elements 7 arranged in a desired pattern, a similarly arranged plurality of jet nozzles 8, and an epithelium support structure 9. The array of incision elements 7 when energized as by release of preloaded springs, are projected out of main body 12 of device 6 to enter the epithelium layer 1 at an inward angle $\alpha$ to the normal of the corneal surface, see FIG. 2c. The distance of projection of incision elements 7 relative to a reference surface 17 engaged on the epithelium, limits the depth of their cut to less than 50 microns so that they cut through most of the epithelium layer, but do not reach the underlying Bowman's layer 2. Incision elements 7 are mounted in a manner to define a tear line for the segment of the epithelium to be removed. In one embodiment, the incision elements are arranged in a circular pattern and, when projected out of body 12, they fully define the tear line. Another embodiment comprises only a few incision elements distributed about a circle, and after the incision is initiated device 6 is rotated about the center of the circle to create a circular tear line.

Figure 2A:
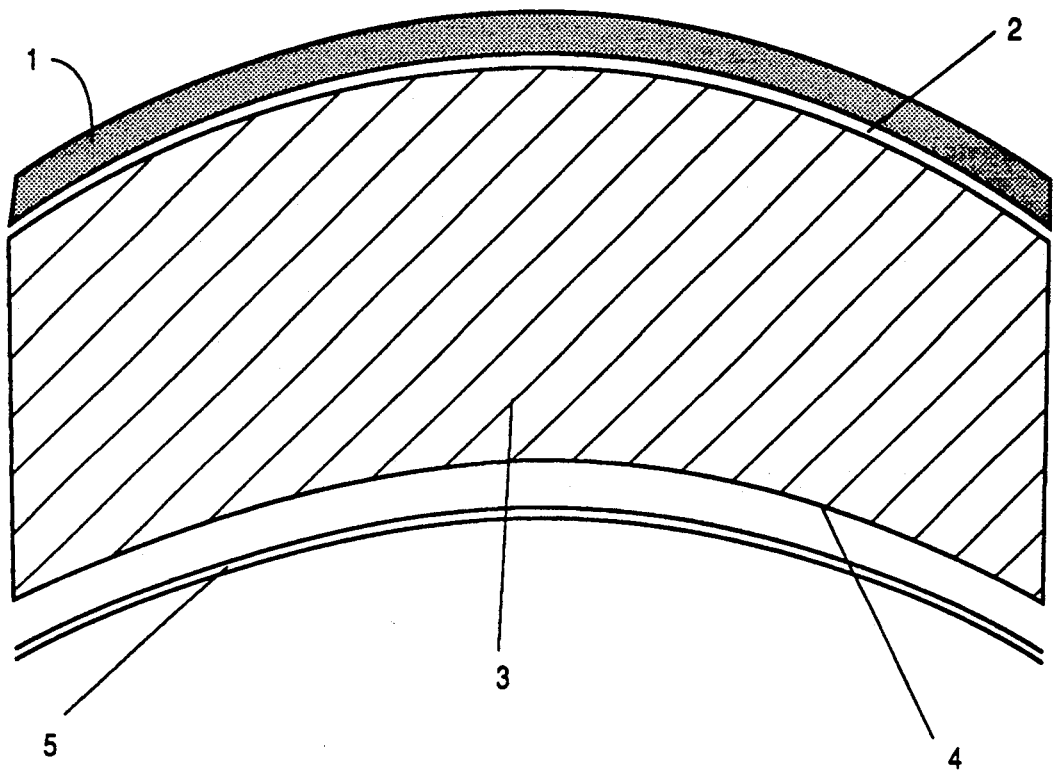
FIG. 2a is a cross-sectional view of the cornea prior to the epithelium lifting procedure.

FIG. 2a shows a cross-sectional view of the eye surface prior to the lifting of the epithelium. The epithelium 1 is attached to Bowman's membrane 2 which is connected to the stroma 3, followed by Descemet's membrane 4, and the endothelium 5. The thickness of these layers is about 540 $\mu$m. The epithelium 1 is approximately 50 $\mu$m thick.

Figure 2B:
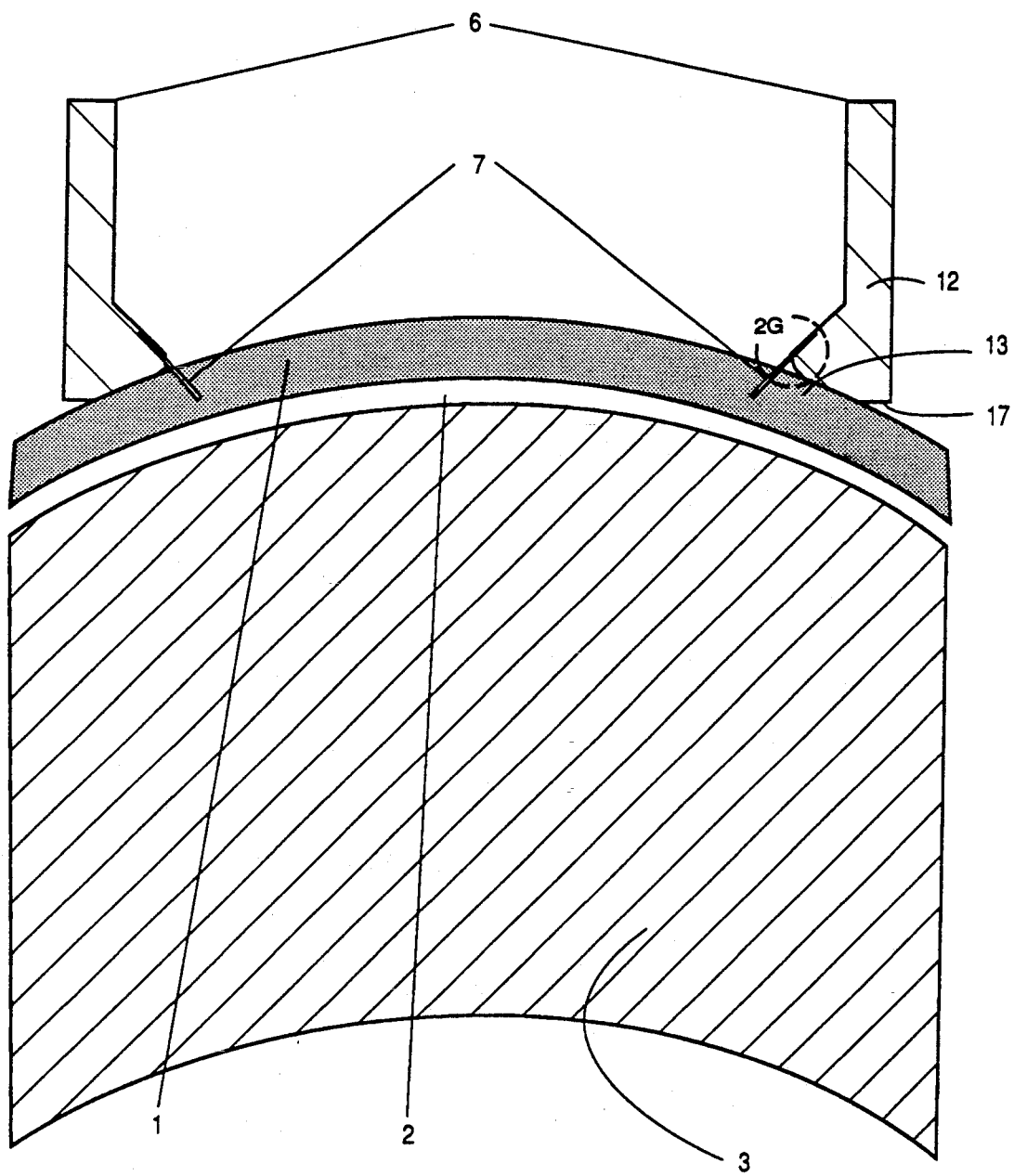
FIG. 2b is a diagrammatic view of creating an incision in the epithelium layer with one component of the device.

In the epithelium lifting process, referring to FIG. 2b, an ophthalmologist places main body 12 of device 6 on the surface of the eye with annular reference surface 17 engaging the epithelium, and initiates the ejection of incision elements 7. The incision elements are ejected by energizing means, such as a prestressed outwardly biased spring 7A, piezoelectric actuators, pneumatic actuators, etc. The incision elements penetrate partially through the epithelium, yet do not reach Bowman's membrane. The limit of their projected movement is established by engagement of suitable stopping surfaces associated respectively with the incision elements 7 and the main body 12.

Figure 2C:
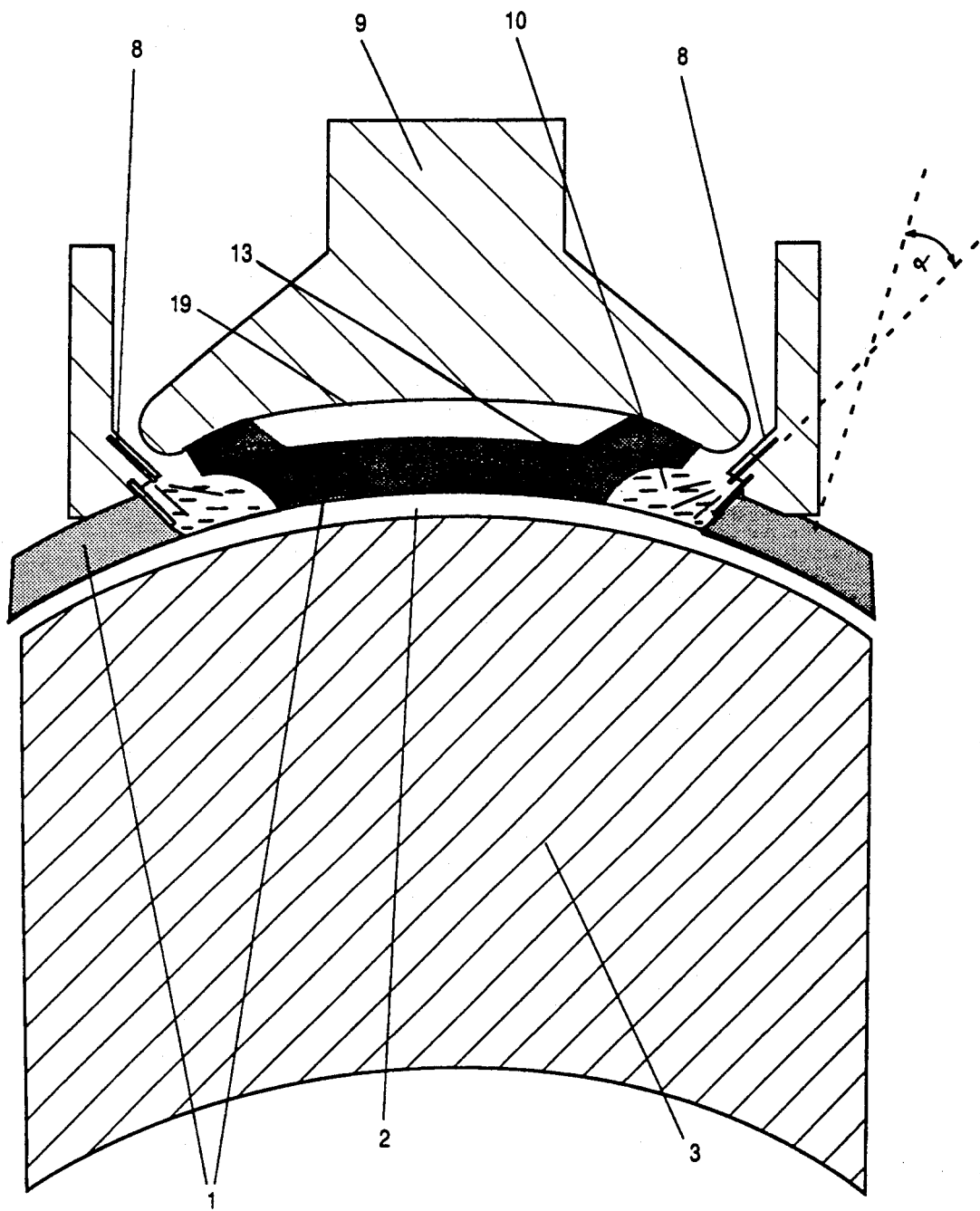
FIG. 2c diagrammatically shows the lifting process using an epithelium support structure of the device.

Referring to FIG. 2c, after the tear line is created, a downwardly directed epithelium support surface 19 provided by support structure 9 is positioned slightly above the anterior surface of a delineated area 13 of the epithelial segment, and jet nozzles 8 are actuated to direct a fluid jet 10 onto the incision tear line formed in the epithelium. Wedging action of the fluid jet 10 causes progressive separation of the epithelium from Bowman's membrane 2 and lifts the epithelium to engage the support surface 19. In one preferred embodiment, support structure 9 comprises a compliant member defining support surface 19. The compliant member (made of silicon rubber, preshaped balloon, etc.) is adapted to yield during the lifting action as the freed segment of the epithelium is forced toward the support surface. The compliance enables progressive advance of the hydraulic wedge formed by the fluid jet.

In another embodiment, the plurality of jet nozzles can be replaced by one ring-form jet nozzle oriented circumferentially around the edge of the tear line and constructed to form a continuous circular jet of fluid directed onto the incision. In both embodiments the direction of the fluid jet is defined by the shape and orientation of jet nozzle 8 which directs the fluid jet in such a manner that its major force has a substantial tangential component related to the corneal surface, directed inwardly relative to the center of the circular tear line. This enables the lifting process to proceed. The relationship between the normal (perpendicular) and tangential components of fluid jet 8, relative to the corneal surface, can be varied as the action proceeds. Advantageously, in the beginning of the lifting process, the fluid jet is directed onto the incision with a strongly predominant normal component, and as the lifting progresses, the tangential component is continuously increased and the normal component decreased to facilitate the wedging action. In one preferred embodiment, incision elements 7 remain extended in place, thus serving to assist in directing the fluid onto the tear line and under the epithelium layer 1; this can increase the fluid wedging action as the fluid slides on the angularly disposed blades of incision elements 7.

Device 6 preferably has several fluid reservoirs, not shown in FIG. 2c, and pressurizing means which pressurize the wedging fluid. Pressure of the fluid supplied to jets 8 is in the range of 1 to 50 bars. The amount of fluid sufficient to perform the operation is a few milliliters. If solutions are used, it is advantageous that they contain additives to maintain balance of electrolytes in the affected tissues.

As the fluid jet 10 progressively moves inward and wedges the epithelium section 13 from the underlying Bowman's layer 2 (or the stroma 3 if there is no Bowman's layer). The portion of the epithelium separated by the fluid moves into supported contact with downwardly directed surface 19 of support structure 9. Thus the support structure 9 preserves its integrity. Even though support structure 9 is brought into close proximity with the epithelium layer to be engaged this layer, it does not limit the separation of the epithelium from the underlying layer. In another embodiment, support structure 9 is constructed to perform a suction action on the epithelium surface to promote the lifting of the epithelium and preserve its structural integrity.

Figure 2D:
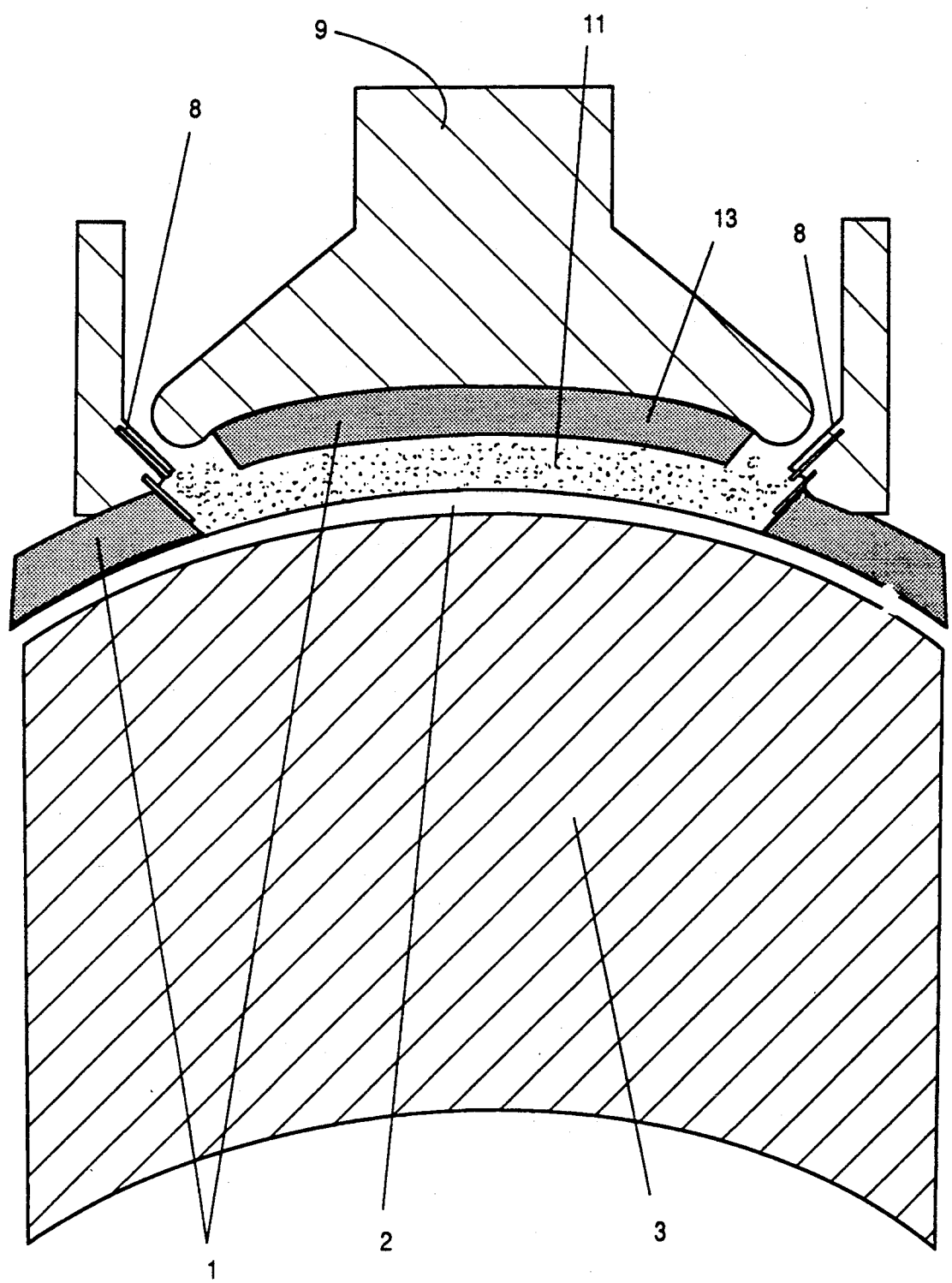
FIG. 2d diagrammatically shows the final stage of the lifting process with the removed section of epithelium held by the epithelium support structure.

Referring to FIG. 2d, after delineated section 13 of the epithelium is completely detached and is held on support structure 9 as by its own slightly adhesive qualities. The removed epithelium is biologically preserved for later use.

Figure 3:
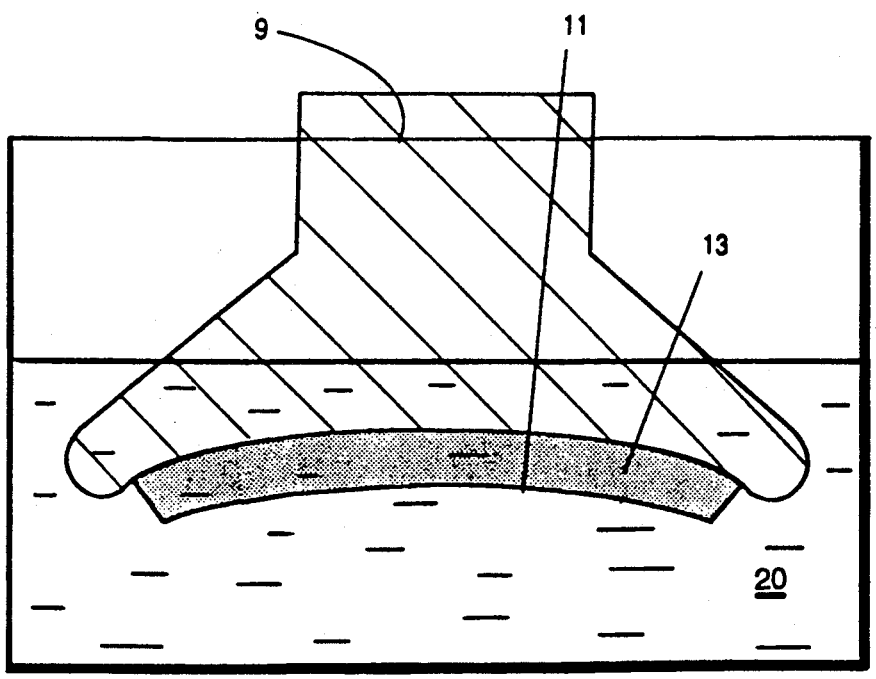
FIG. 3 is a diagrammatic cross-sectional view of the lifted epithelium stored in an agent.

The presence of a support during the wedging action of the fluid is important when it is desired to preserve the lifted epithelium as the support tends to prevent tearing of the epithelium being lifted from the underlining Bowman's membrane. The subsequent biological preservation of the lifted epithelium is achieved by storing it in an agent 20 which does not significantly alter the biological function of the epithelium cells, as shown in FIG. 3.

Figure 2E:
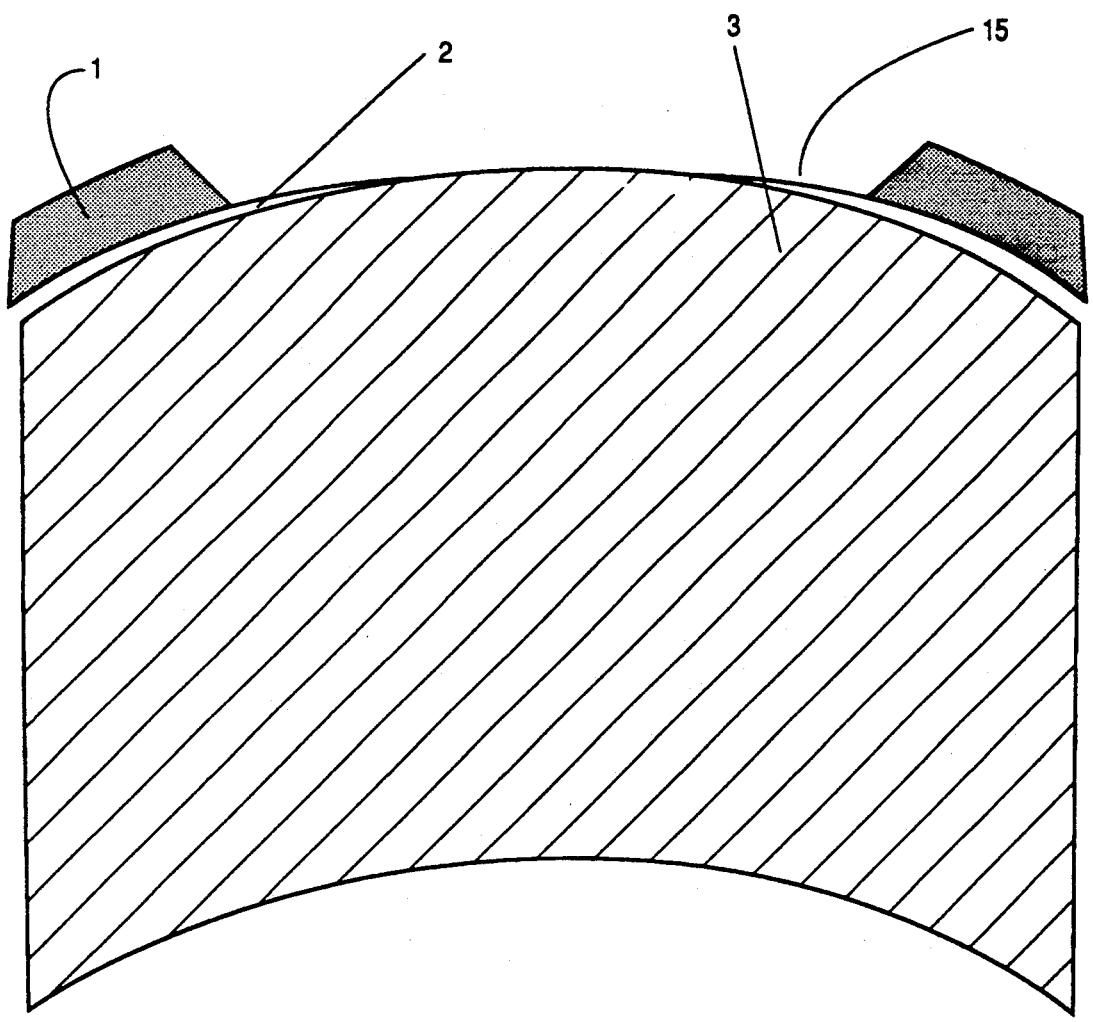
FIG. 2e is a cross-sectional view of the cornea after lifting the epithelium and after a sculpting procedure has been performed to re-shape the stroma.
Figure 2F:
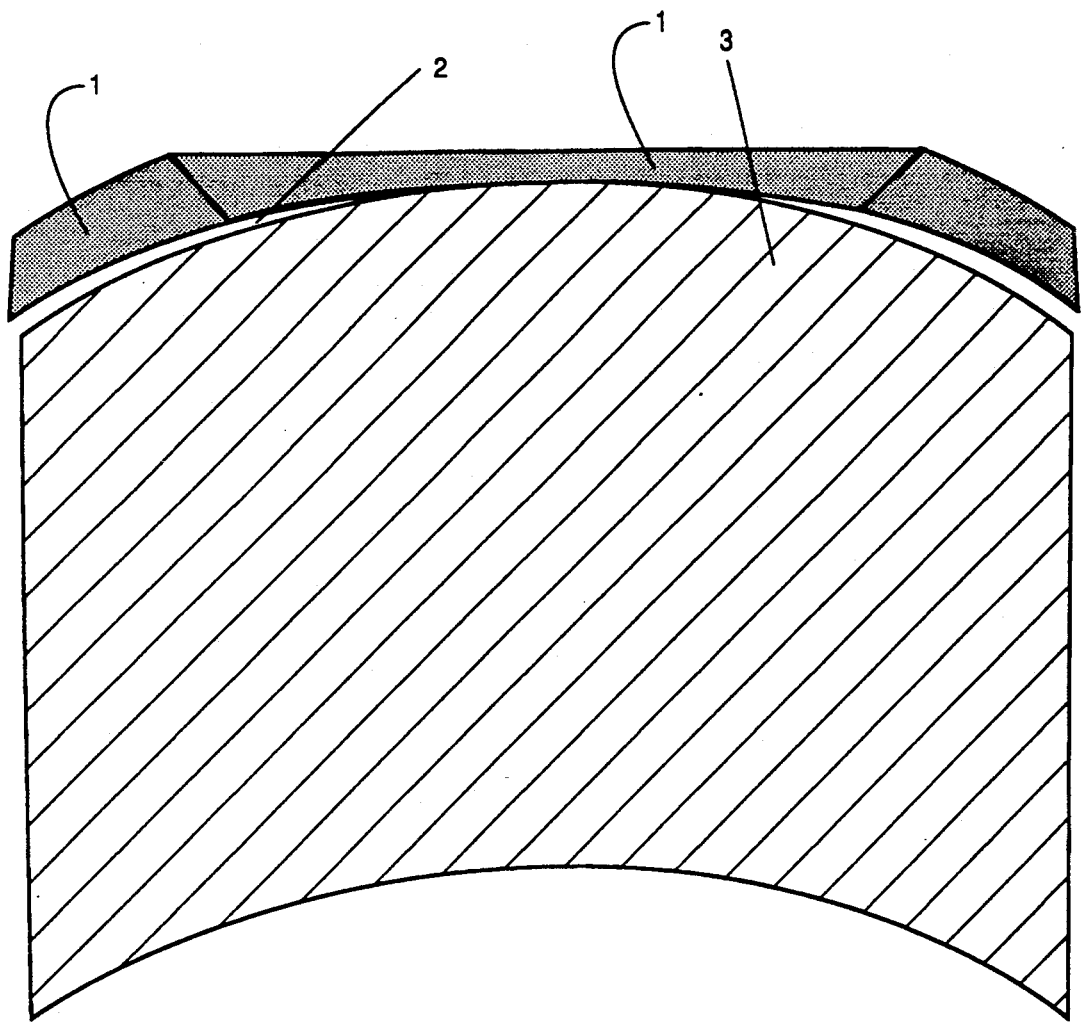
FIG. 2f is a cross-sectional view of the cornea after the lifted section of the epithelium has been repositioned on the re-shaped stroma.
Figure 2G:
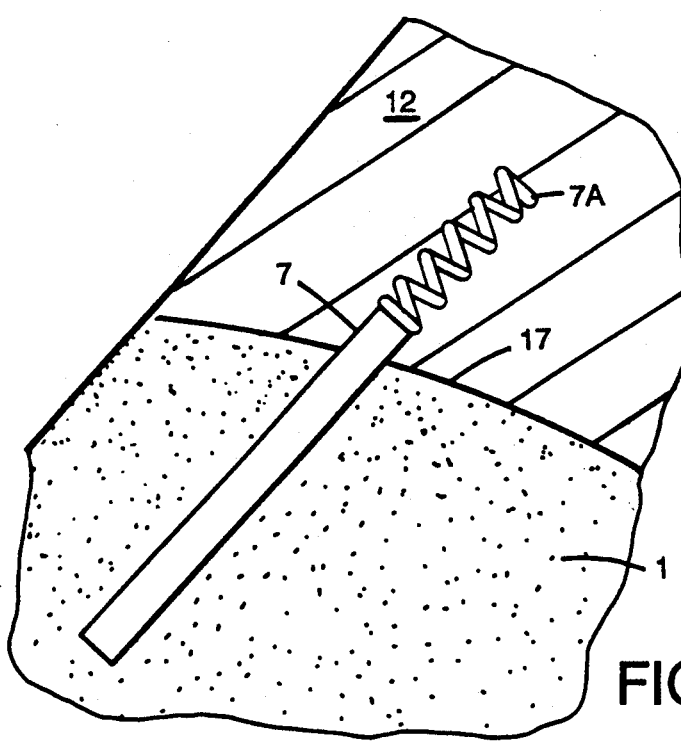
FIG. 2g is a diagrammatic cross-sectional view of region 2g, shown in FIG. 2b, displaying an outwardly biased spring connected to the incision instrument.

Referring to FIG. 2e, an exposed surface 15 of the eye is operated upon, as done by corneal surgeries of various kinds. After the surgery is completed, the removed section of the epithelium is placed back on the exposed surface of the eye, as shown in FIG. 2f.

The removed layer of epithelium can be repositioned on the exposed surface of the eye either by using support structure 9 or by removing the epithelium from the support structure 9 and using another instrument designed for the repositioning of the epithelium. The finger of the surgeon can also be used to place the removed layer of epithelium back on the eye in a manner similar to the manner in which a contact lens is placed onto the eye surface. The repositioned epithelium may reattach itself on the exposed corneal surface or serve as a biologically compatible shield to promote regrowth of the epithelium cells.

As mentioned above, preferably, epithelium lifting device 6 has several reservoirs for storing fluids used in the lifting process. If liquid is used to separate the epithelium, it is preferable to use an isotonic solution, i.e., a solution which possesses the same osmotic pressure as the cells of the underlying layer, so that neither swelling nor shrinking of the cells of the Bowman's layer or the stroma occurs. The solution may be one or a mixture of isotonic solutions that are commercially available, such as: GBR glutathione bicarbonate ringer, BSS balanced salt solution, BSSPlus balanced salt solution plus, or LRS lactated ringer's solution.

As previously mentioned, for some patients, it is very difficult to separate the epithelium layer from the underlying layer which is the Bowman's membrane or the stroma. This is especially true for contact lens wearers or for people who previously underwent laser sculpturing of the surface of their eye. In these patients the regrown epithelium is of high strength, so that it is difficult to detach the epithelium. Advantageously, according to the invention, bond weakening agents, for example, ethyl alcohol or cocaine hydrochloride, are applied prior to the lifting action. The bond weakening agents are applied to the epithelium by a dosing system, which can control their timing and action. Whereas, in general, disadvantages of bond weakening agents are that they dissolve the cells and rapidly flow throughout the epithelium, and thus it is difficult to limit their application only to the selected regions which are planned to be removed. However, this need not be the case with the present invention. In the procedure of the present invention, the distribution of a bond weakening agent can be of quite limited duration to delineated region 13 since the lifting action takes only a few seconds. Even though a bond weakening agent might dissolve the epithelium cells of the removed epithelium layer, its use can still be advantageous in enabling detachment of the epithelial layer which otherwise would not be smoothly unremovable.

ALTERNATIVE EMBODIMENTS

In another embodiment, wherein the preservation of the epithelium layer is not desired, support structure 9 is not used. Here, the fluid jets remove the epithelium which in the lifting process may be destroyed.

There are several alternative embodiments of the jet nozzles. During the lifting process, the nozzles can remain stationary or can move around the incision pattern to improve the wedging action of the fluid.

In another embodiment, the incision element has microhooks located on their cutting edges. After the incision is formed, the incision elements are rotated, so that the microhooks create a tangential cut and initiate the separation of the epithelium from the underlying layer and start the tearing-off process.

In another embodiment, the bond weakening agents stored in a reservoir are injected into the incision area by additional nozzles.

EXAMPLE

The process of epithelium lifting with a fluid jet has been tested on numerous freshly removed pig eyes. All initial experiments were performed with devices which had only a single jet. In the epithelium lifting process two types of tests were performed. The first test was designed to assess the efficacy of various fluids. The jet nozzles were made from hypodermic needles of various diameters (from 100 to 500 $\mu$m). The jets were adapted to eject either water or air to lift the epithelium. Currently, better results have been obtained using water as the wedging medium, since in the single jet arrangement water expressed a much more pronounced ability to lift the epithelium.

In the second set of experiments the water pressure ejected from the jet and the nozzle diameter of the jet were varied. Faster epithelial lifting occurred with rising water pressure up to 7 Bar. By suitable trial, jet parameters for each described embodiment will be realized, depending upon their member and the specific nature of their design.

What is claimed is:

1. A method of removing the epithelium from a selected area of the eye comprising the steps of:
   (a) cutting the epithelium in the direction of its thickness in a peripheral pattern circumscribing the selected area of epithelium to be removed,
   (b) producing a fluid jet having sufficient force to effectively wedge said epithelium free form the relatively hard underlying layer to which said epithelium is biologically attached,
   (c) directing said jet through said cut pattern in the epithelium in the manner that the fluid progresses inwardly from said peripheral pattern between the epithelium and the relatively hard underlying layer to which said epithelium is biologically attached to effectively wedge said epithelium, by force of the fluid, free from said underlying layer.

2. The method of claim 1 including simultaneously directing said fluid inwardly at regions distributed about said peripheral pattern.

3. A method of removing the epithelium from a selected area of the eye comprising the steps of:
   (a) cutting the epithelium in the direction of its thickness in a peripheral pattern circumscribing the selected area of epithelium to be removed,
   (b) producing a fluid jet having sufficient force to effectively wedge said epithelium free from the relatively hard underlying layer to which said epithelium is biologically attached,
   (c) directing said jet through said cut pattern in the epithelium in the manner that the fluid progresses inwardly from said peripheral pattern between the epithelium and the relatively hard underlying layer to which said epithelium is biologically attached to effectively wedge said epithelium, by the force of the fluid, free from said underlying layer, and
   (d) engaging an exterior surface of the selected area of the epithelium in a manner supporting and maintaining, at least partially, the structural integrity of said epithelium freed from said underlying layer.

4. The method of claim 3 including biologically preserving the freed, structurally intact segment of epithelium while a medical procedure is conducted on the exposed eye and thereafter returning said epithelium segment onto the eye in a manner to cause it to reattach as living cells integrated with the eye.

5. The method of claim 3 including holding a support surface immediately adjacent the outer surface of said selected area of epithelium while said fluid jet is applied in the manner that the freed segment of epithelium is supported by said support surface.

6. A method of eye surgery comprising employing the method of claim 4 to lift and preserve the epithelium, conducting a surgical operation on the thus exposed eye and after completion of said surgery, replacing the lifted epithelium upon said eye over the region where the surgery was conducted.

7. A method of removing biologically attached epithelium from a selected surface area of the eye comprising the steps of:
   (a) providing a jet assembly constructed to produce an epithelium-detaching fluid jet capable of detaching epithelium that is biologically attached to an underlying structure of the eye,
   (b) directing the epithelium-detaching fluid jet at said area in the manner that force of said jet is substantially tangential to the eye surface, whereby the force of said fluid separates and removes the epithelium from the relatively hard underlying layer to which it is biologically attached.

* * * * *